United States Patent [19]
Angelillo et al.

[11] Patent Number: 5,736,110
[45] Date of Patent: Apr. 7, 1998

[54] ACTIVATOR FOR INITIATING CRYSTALLIZATION OF A SUPERSATURATED SOLUTION

[76] Inventors: Stephen P. Angelillo, P.O. Box 493000, Leesburg, Fla. 34749-30000; Robert H. Birdsey, 4205 Wood Dr., Mount Dora, Fla. 32757

[21] Appl. No.: 644,429

[22] Filed: May 10, 1996

Related U.S. Application Data

[63] Continuation of Ser. No. 442,172, May 16, 1995, abandoned.

[51] Int. Cl.$^6$ .................................................. F24J 1/00
[52] U.S. Cl. ........................... 422/245.1; 126/263.04
[58] Field of Search ............... 422/245.1; 126/263.03, 126/263.04, 261.02

[56] References Cited

U.S. PATENT DOCUMENTS

| | | | |
|---|---|---|---|
| 708,549 | 9/1902 | Heiliger | 126/263.04 |
| 811,750 | 2/1906 | Spieske . | |
| 1,384,747 | 7/1921 | Eckelmann et al. . | |
| 1,385,074 | 7/1921 | Ferguson . | |
| 1,656,366 | 1/1928 | Sterling et al. . | |
| 1,915,523 | 6/1933 | Ferguson . | |
| 1,920,853 | 8/1933 | Ferguson . | |
| 2,157,169 | 5/1939 | Foster . | |
| 2,220,777 | 11/1940 | Othmer . | |
| 2,289,425 | 7/1942 | Hogan . | |
| 2,386,654 | 10/1945 | Caldwell . | |
| 2,827,438 | 3/1958 | Broadley et al. . | |
| 2,907,173 | 10/1959 | Robbins . | |
| 3,223,081 | 12/1965 | Hunt . | |
| 3,475,239 | 10/1969 | Fearon et al. . | |
| 3,585,982 | 6/1971 | Hollinshead . | |
| 3,804,077 | 4/1974 | Williams . | |
| 4,057,047 | 11/1977 | Gossett . | |
| 4,077,390 | 3/1978 | Stanley et al. . | |
| 4,142,508 | 3/1979 | Watson . | |
| 4,379,448 | 4/1983 | Kapralis . | |
| 4,460,546 | 7/1984 | Kapralis . | |
| 4,532,110 | 7/1985 | Kapralis . | |
| 4,559,047 | 12/1985 | Kapralis et al. . | |
| 4,580,547 | 4/1986 | Kapralis et al. . | |
| 4,829,980 | 5/1989 | Smith . | |
| 4,860,729 | 8/1989 | Benson et al. . | |
| 4,872,442 | 10/1989 | Manker . | |
| 4,880,953 | 11/1989 | Manker . | |
| 4,899,727 | 2/1990 | Kapralis et al. . | |
| 4,916,922 | 4/1990 | Mullens . | |
| 5,056,589 | 10/1991 | Hettel et al. . | |
| 5,058,563 | 10/1991 | Manker . | |
| 5,143,048 | 9/1992 | Cheney, III | 422/245.1 |
| 5,205,278 | 4/1993 | Wang | 422/245.1 |
| 5,339,796 | 8/1994 | Manker . | |

*Primary Examiner*—Robert Kunemund
*Attorney, Agent, or Firm*—Frijouf, Rust & Pyle, P.A.

[57] ABSTRACT

An improved activator and method is disclosed for initiating crystallization of a supersaturated solution within a flexible container. The activator comprises a flexible screen for immersing in the supersaturated solution within the flexible container. The flexible screen defines a plurality of apertures therein with an activation material being affixed to the screen within the plurality of apertures. Upon flexing of the flexible screen by an operator, the activation material interacts with the screen to initiate crystallization of the supersaturated solution.

18 Claims, 3 Drawing Sheets

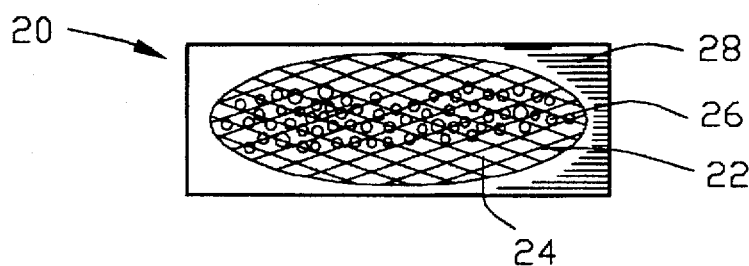
FIG. 5
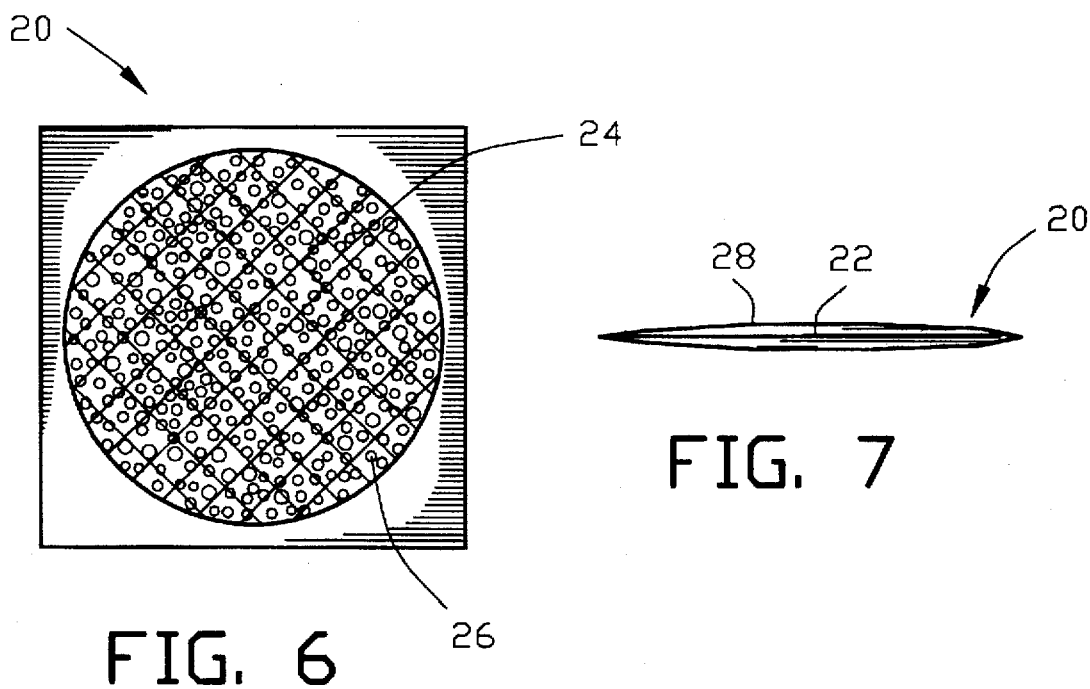
FIG. 6
FIG. 7
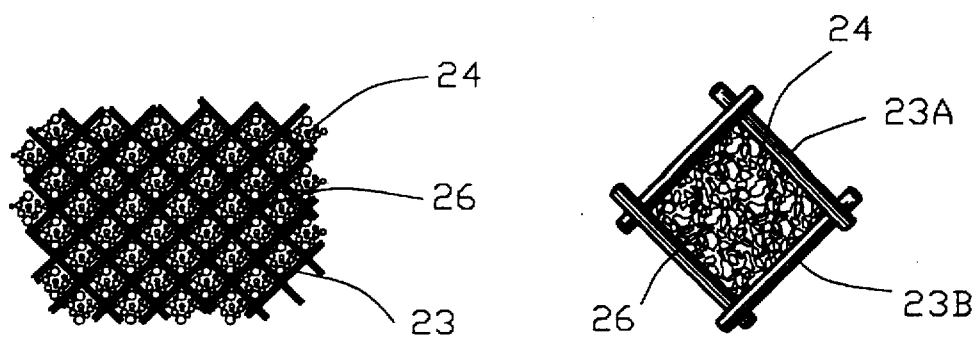
FIG. 8
FIG. 9

5,736,110

1

ACTIVATOR FOR INITIATING CRYSTALLIZATION OF A SUPERSATURATED SOLUTION

This application is a continuation of application Ser. No. 08/442,172, filed May 16, 1995, now abandoned the disclosure of which is incorporated herein by reference.

BACKGROUND OF THE INVENTION

1. Field of the Invention

This invention relates to thermal packs containing a supersaturated solution, and more specifically to an activator and a method for making the activator for initiating crystallization of a supersaturated solution.

2. Background of the Invention

Portable thermal packs have long been recognized as a useful and convenient source of heat where access to flame or electric heat was impractical or inconvenient. An early example of such a heat pack was the hot water bottle wherein a hot liquid was placed in a container. Heat from the hot liquid within the hot water bottle was then transferred through the wall of the container to the desired heat-receiving location.

Unfortunately, hot water bottles and like devices immediately began to cool as soon as the hot liquid was placed in a container. If the hot water bottle was required over a period of several hours of use, a significant portion of the heat was lost in the first hour of use.

A later example of a heat pack based upon the well known principal that heat is released upon the crystallization of the supersaturated solution. If the initiation of that crystallization could be "triggered" by an operator, heating of the device could be delayed until the heat was desired thereby greatly improving the effectiveness of the device. Many such heat storing devices, and the activators which initiated the crystallization, were developed by the prior art.

U.S. Pat. No. 811,750 to Spieske discloses a heat-storing compound consisting of acetate of soda and chloride of calcium.

U.S. Pat. No. 1,384,747 to Eckelmann et. al. discloses a chemical heater comprising a container, a crystallizable salt solution and a sealing material adapted to be melted when heated in the container, the sealing material being of less specific gravity than that of the salt solution and adapted to solidify upon cooling and to form a seal preventing crystallization while the seal remains intact, and a device normally extending through the seal and into the salt solution and adapted upon withdrawal to rupture the seal and cause the salt solution to crystallize.

U.S. Pat. No. 1,385,074 to Ferguson discloses a container and a solution of a crystallizable salt and a sealing means in the container, the sealing means being of a lesser specific gravity than the salt solution and adapted to be melted upon application of heat thereto and float upon the surface of the salt solution and, upon cooling, to solidify and adhere to the walls of the container and in engagement with the surface of the salt solution, preventing relative movement and crystallization thereof regardless of the position of the container.

U.S. Pat. No. 1,656,366 to Crooker discloses an unstable solution yielding heat on crystallization comprising sodium acetate, calcium chloride and water, the proportion of water being 46% of the total.

U.S. Pat. No. 1,915,523 to Ferguson discloses a chemical heater comprising a flask partially filled with a chemical, normally liquid, but which crystallizes upon contact with air with evolution of heat, a valve closure comprising seat structure in the wall of the flask, a valve seating externally on the seat structure, a valve stem projecting inwardly from the valve and adapted to be contacted by the liquid, and a spring for closing the valve, surrounding the valve stem and held in compression against an abutment on the stem, the helices of the spring closely embracing the stem in wiping contact therewith for initiating crystallization of the liquid chemical.

U.S. Pat. No. 1,920,853 to Ferguson discloses a heat flask comprising a casing, means in the casing having the property of changing its state with evolution of heat when contacted by air, the casing being provided with valve structure for controlling the admission of air to the casing, the valve structure comprising a shell having an external valve seat, and an annular edge at its inner end, a stem reciprocally mounted in the shell and extending therethrough, having a valve engaging the seat and having a flared inner end extending beyond the shell adapted to engage the inner end of the shell in valve relation when the external valve is opened, the stem and shell providing an air passage and the interior of the casing in intermediate positions of the valve stem, a spring mounted in the shell normally holding the external valve closed, the means for operating the valve.

U.S. Pat. No. 2,157,169 to Foster discloses a heat bag of the character described including an envelope of canvas or the like having therein a compartment containing one ingredient of a heat productive chemical mixture in granular form, and a bag of paper or the like contained within the envelope, the bag containing another ingredient of such a heat productive mixture in granular form, and the bag being constructed and arranged to be readily frangible by the user to enable the ingredients to be mixed within the envelope.

U.S. Pat. No. 2,220,777 to Othmer discloses a closed and hermetically sealed chemical heater formed of a substantially rigid metal shell having an integral flexible diaphragm and which includes a supersaturated salt solution within the heater which causes the temperature of the unit to rise when crystallized, and means which upon manual manipulation of the flexible diaphragm without opening the container are adapted to cause a metal to metal friction within the container, thereby crystallizing the solution.

U.S. Pat. No. 2,289,425 to Hogan discloses a device of the character described comprising a container charged with a liquid composition containing a crystallizable compound, the composition being capable of releasing heat by crystallization of the compound, a discharging unit, and a permanent crystal of the compound carried by the unit, the unit being manually operable to bring the crystal into contact with the composition to cause crystallization of the compound.

U.S. Pat. No. 2,386,654 to Caldwell discloses a chemical immersion heater comprising a container having venting means at its upper end communication with the exterior thereof, a charge compacted in the lower end of the container including a heating composition comprising at least in part a packed mixture of solid ingredients adapted on ignition to react exothermically to yield a molten slag as the principal product of their reaction, a spacer body adapted to permit gas to flow past it, supported by and in direct contact with the heating composition, and a gas permeable cooling filter interposed between the spacer body and the venting means, and comprising a mass of loose incombustible material pressed into the form of a plug, completely filling the upper end of the container immediately below the venting means and supported by the spacer body.

U.S. Pat. No. 2,827,438 to Broadley et. al. discloses a heat storage medium which reversibly acquires substantial content of solid crystalline disodium phosphate dodecahydrate and assumes substantially completely liquid solution form within a predetermined, reproducible range of transition temperature respectively upon release of heat therefrom and absorption of heat therein consisting essential of one hundred parts by weight of disodium phosphate, water in amount from 150 to 260 parts by weight, trisodium phosphate sufficient to bring the resulting mixture to pH of 8.3 to 9.6 and carbon in amount less than 50 parts by weight.

U.S. Pat. No. 3,223,081 to Hunt discloses a bottom-hole heater for oil wells having in combination an elongated cylindrical enclosed vessel, a catalyst chamber therein, a fluid-tight jacket about the vessel defining an enclosed space between the jacket and the vessel, and a conduit extending into the chamber to form an annular space in the chamber and an annular opening at the top thereof, a fuel oxidation catalyst in the chamber, and heat transfer material in the enclosed space to remove heat from the chamber via the jacket.

U.S. Pat. No. 3,475,239 to Fearon et. al. discloses exothermic compositions comprising a particulate oxide of an alkali metal or alkaline earth metal and a solid, particulate acid or strongly acid salt. The alkaline oxide is present in the composition in an amount sufficient to at least neutralize the acidic reactant, and preferably in an amount in excess of the theoretical amount required for neutralization. The exothermic compositions of this invention are useful in a plurality of applications wherein a controlled amount of heat is desired, such as curing of resinous materials, heating of foods, defrosting of frozen articles and other similar applications. Packages are also provided which are adapted to hold the alkaline oxide reactant and acidic reactant separately from each other until immediately before use, whereupon the oxide and acidic reactants are blended together in the package, which is then secured to the object to be heated, for example, a pipe joint, and the exothermic reaction is initiated by injecting a small amount of water into the exothermic composition.

U.S. Pat. No. 4,077,390 to Topanga discloses a heat pack made by enclosing supercoolable aqueous sodium acetate solution together with a metallic activator strip in a sealed, flexible container. The activator strip is a flexible metal strip having one or more fissures or slits extending therethrough. To prepare the heat pack for activation, its contents are first heated to a temperature above the melting point of sodium acetate to completely melt it. Thereafter, the sodium acetate solution is supercooled. Activation or crystallization of the sodium acetate (with evolution of heat) is produced by bending the activator strip.

U.S. Pat. No. 4,142,508 to Watson discloses a method for splicing cables whereon a first cable is connected to a second cable to form a junction and a heat shrinkable sleeve is positioned over the junction. A portable hot pack having properties for developing a temperature in excess of 250° C. is conformed around the sleeve to shrink the sleeve around the junction and thereby seal and insulate the junction. The hot pack can include first and second chemicals which react to initiate a series of heat producing reactions which occur at different temperatures to incrementally elevate the temperature of the hot pack.

U.S. Pat. No. 4,379,448 to Kapralls et. al. discloses a trigger to initiate crystallization of a supercoated salt solution comprising a thin strip having a perimeter with the strip having a multiplicity of slits formed therein, each slit characterized as having opposed elongated edges which face one another in near touching relation. The strip is further characterized as having two configurations between which it is bendable with snap-displacement causing the slit edges to initiate progressive exothermic crystallization of the salt in the solution.

U.S. Pat. No. 4,460,546 to Kapralls et. al. discloses a trigger usable in initiating crystallization of a supercooled salt solution comprising a thin metallic strip containing multiple pin-hole size openings, and which is bendable with snap displacement. The strip may typically be non-ferrous.

U.S. Pat. No. 4,532,110 to Kapralls et. al. discloses a protected trigger usable in initiating crystallization of a supercooled salt solution comprising a thin metallic strip containing multiple openings. The strip is protected by a peripheral frame and/or by a metallic coating.

U.S. Pat. No. 4,559,047 to Kapralls et. al. discloses a flexible mask that includes a container for triggering of salt crystallization. The mask is manipulated to prevent stiffening, so as to be closely fitted to a human face to transmit heat thereto for therapeutic purposes.

U.S. Pat. No. 4,580,547 to Kapralls et. al. discloses a heat producing apparatus that includes a plastic container having flexible walls which are interconnected along a linear zone with a supercooled salt solution being in the container to be triggered and crystallized to produce heat. A trigger floats in the solution relative to the linear zone and includes a bendable trigger strip and a multiple member frame confining the strip.

U.S. Pat. No. 4,829,980 to Smith discloses a trigger device for a heat pack comprising three helically-coiled, resilient metallic filaments nested one within the other and of inwardly decreasing diameter, the filament being wound in a sense opposite to that of filaments (1) and (3). Flexing the assembly of nested helices about its longitudinal axes produces a rubbing action between adjacent turns thereof which initiates crystallization. Other devices comprise two nested helices wound in the same sense; a single helix having a pressure plate at one end and an external or internal cap at the other; and a body of randomly convoluted or woven metallic filament.

U.S. Pat. No. 4,872,442 to Manker discloses an activator for reliably initiating crystallization of a super-cooled aqueous salt solution, the activator being formed of a flexible, relatively thin metal, having at least one slit extending therethrough and with the opposing sides of the slit being in contact along at least a part of the length of the slit, and the activator having a number of minute metal nodules attached to and protruding from the surface thereof and adjacent to the slit, the nodules being adapted to be detached from the surface upon flexing of the activator.

U.S. Pat. No. 4,880,953 to Manker discloses a method of recharging or regenerating a substantially solid spent heat pack of the type in which a super-coolable salt solution is confined within a flexible plastic pouch and converted to solid form with evolution of heat, by contacting the solid contents of the pack with a source of microwave energy sufficient to melt the solid to the liquid state, without thereby damaging the heat pack.

U.S. Pat. No. 4,899,727 to Kapralls et. al. discloses an economically fabricated trigger for initiating crystallization of supercooled solutions in flexible plastic containers, the trigger comprising a thin substantially imperforate metallic strip having a perimeter bounding a generally dish-shaped or concave portion, the strip further having a plurality of spaced, generally parallel, generally V-shaped elongated grooves formed inwardly from the perimeter, the strip being imperforate at the groove, with the centermost portion substantially free of grooves, the strip having two configurations between which it is distortable or bendable with snap-displacement causing the initiation of progressive exothermic crystallization of the salt in the solution. The strip metal is typically impacted during fabrication to orient the molecular structure so as to aid the functioning of the disc or strip to produce or initiate crystallization.

U.S. Pat. No. 5,056,589 to Hettel et. al. discloses a self-contained manually triggerable thermal energy pack that includes a flexible enclosure containing a supercooled solution capable of being triggered to begin crystallization and a triggering structure including a single close turn helical metallic spring having sufficient stiffness to maintain its cylindrical shape and sufficient resiliency to allow bending by the application of manual pressure normal to its axis.

U.S. Pat. No. 5,058,563 to Manker discloses reusable warmers of the supersaturated solution type that are substantially free of saddlebagging. The reusable warmers comprise a flexible container, and are located within the container, a supercooled salt solution, an activator for initiating crystallization of the supercooled salt solution, and a gelling agent, the gelling agent being present in sufficient quantity to convert the salt solution to a gel.

U.S. Pat. No. 5,339,796 to Manker discloses reusable warmers of the supersaturated solution type that are substantially free of saddlebagging. The warmers also exhibit a more sustained period of time during which the heat pack remains within a therapeutically useful temperature range. The reusable warmers of the present invention also maintain a substantial degree of flexibility during their useful heat cycle. The reusable warmers comprise a flexible container, and are located within the container, a supercooled salt solution, an activator for initiating crystallization of the supercooled salt solution, and a gelling agent, the gelling agent being present in sufficient quantity to convert the salt solution to a gel.

Although each of these devices significantly advanced the art of portable heating, each of these devices also suffers from certain shortcomings especially in the triggering device. Some of the triggering devices are complicated devices and accordingly raised production costs. Some triggering devices were not effective in initiating crystallization while other triggering devices were not reliable and would initiate crystallization inadvertently or prematurely during manufacture, shipping or handling. Other of these triggering devices were not easy to operate requiring a dozen or more flexes to initiate crystallization.

Therefore, it is a primary object of the present invention to provide an improved activator for initiating crystallization of a supersaturated solution with improved capabilities and which provides a significant advance in the art.

Another object of this invention to provide an improved activator for initiating crystallization of a supersaturated solution that is simple to operate.

Another object of this invention to provide an improved activator for initiating crystallization of a supersaturated solution that is manufactured through a simple and low cost process.

Another object of this invention to provide an improved activator for initiating crystallization of a supersaturated solution that is effective in producing crystallization.

Another object of this invention to provide an improved activator for initiating crystallization of a supersaturated solution that is reliable in effecting crystallization upon demand, and inhibiting crystallization inadvertently.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved activator for initiating crystallization of a supersaturated solution within a flexible container. The activator comprises a flexible screen for immersing in the supersaturated solution within the flexible container. The flexible screen defines a plurality of apertures therein. An activation material is affixed to the screen within the plurality of apertures. The activation material interacts with the screen to initiate crystallization of the supersaturated solution upon flexing of the flexible screen.

In one example of the invention, the screen comprises a plurality of interwoven strands having a warp and a weave. The screen and the activation material define a plurality of contact interfaces therebetween for creating a shearing action between the screen and the activation material upon flexing of the screen. At least one of the abrasive particles has contact interfaces with at least two of the strands of the screen preferably a warp and a weave of the screen. Preferably, a plurality of contact interfaces define a plurality of planes for allowing non-parallel forces to be simultaneously exerted by the screen on the activation material upon flexing of the screen. In a more specific example of the invention, the screen is of a size of not less than 40 and not greater than 50 mesh.

Preferably, an adhesive agent adheres the activation material to the screen. A lamination is affixed to the screen for inhibiting the initiation of crystallization. In one embodiment of the invention, the lamination includes a tape disposed on opposed sides of the screen. The activation material comprises a plurality of abrasive particles. In one example of the invention, the activation material comprises particles having a diameter not larger than one third the diameter of the apertures and not smaller than one fifteenth the diameter of the apertures. The activation material comprises particles having a size of not larger than 120 grit and not smaller than 600 grit with a hardness of six or greater on the Mohs scale.

The invention also resides in the method of making an improved activator for initiating crystallization of a supersaturated solution in a flexible container, comprising the steps of cutting a slug from a screen and placing the slug in a sodium silicate solution. Excess sodium silicate solution is drained from the slug and the slug is placed into a shaker containing an abrasive particulate. The shaker is agitated and the slug is removed to mechanically press the abrasive particulate tightly into the slug. The slug is dried and is laminated with a polymeric material.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 5 is an isometric view of the improved activator;

FIG. 6 is a top view of the improved activator of FIG. 5;

FIG. 7 is a bottom view of the improved activator of FIG. 6;

FIG. 8 is an enlarged view of a portion of FIG. 6 illustrating the activation material affixed to the screen;

FIG. 9 is an enlarged view of a portion of FIG. 8 illustrating four adjacent strands of the screen and the activation material therebetween;

Similar reference characters refer to similar parts throughout the several Figures of the drawings.

DETAILED DISCUSSION

Figure 1:
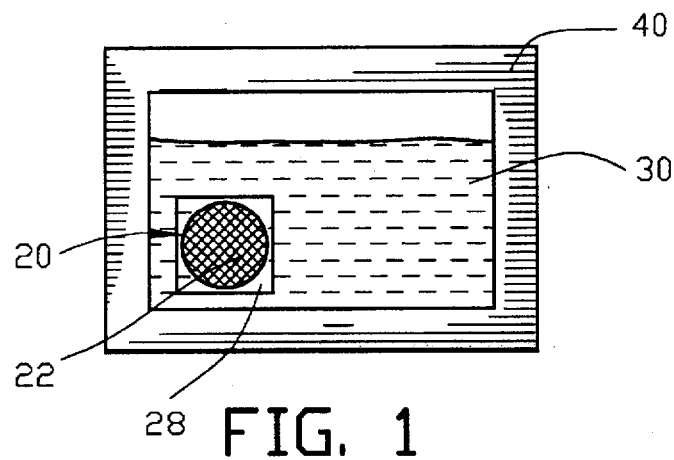
FIG. 1 is an elevational view of an improved activator immersed in a supersaturated solution contained within a flexible container.

FIG. 1 is a top view of an improved activator 20 immersed in a supersaturated solution 30. Both the activator 20 and the solution 30 are contained within a flexible container 40.

Figure 2:
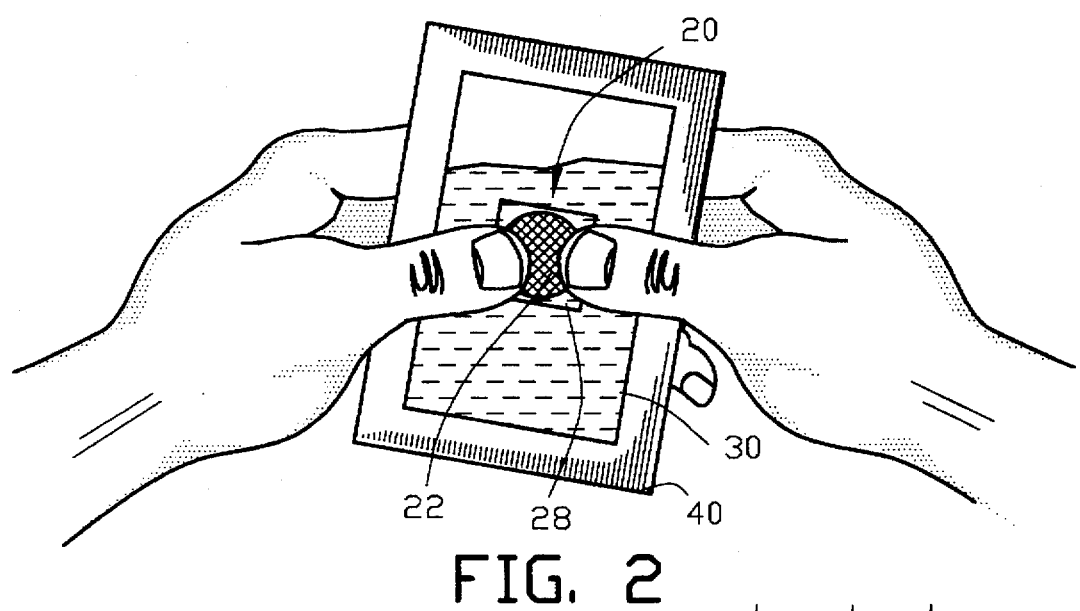
FIG. 2 is an elevational view illustrating the flexing of the activator within the flexible container by an operator.
Figure 3:
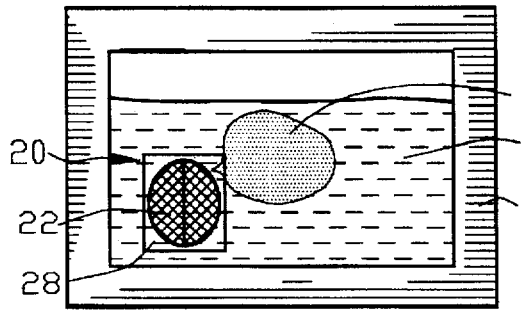
FIG. 3 is an elevational view similar to FIG. 1 illustrating the initiation of crystallization of the supersaturated solution.
Figure 4:
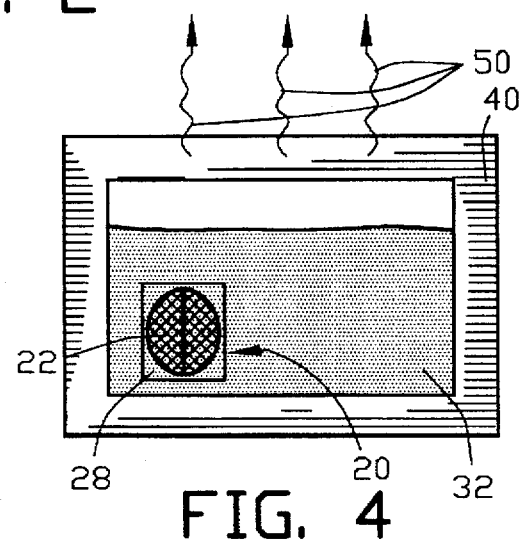
FIG. 4 is an elevational view similar to FIG. 1 illustrating the release of heat upon crystallization of the supersaturated solution.

FIGS. 2–4 are elevational views illustrating the process by which the activator 20 initiates the formation of crystals 32 from the solution 30, resulting in the release of heat 50, as described more fully hereinafter.

FIGS. 5–7 are various views of the activator 20, which comprises a screen 22, activation material shown as a plurality of abrasive particles 26, with a lamination 28 enclosing the screen 22.

The screen 22 is comprised of a plurality of interwoven strands 23 normally referred to as the warp 23A and the weave 23B. In the preferred embodiment, the strands 23 are of 316 stainless steel composition, but other metals including copper and bronze may be used with the invention. As best shown in the enlarged views of FIGS. 8 and 9, the interwoven strands 23 define a plurality of apertures 24 in the screen 22. The size or "mesh" of the screen 22 is determined by the number of apertures 24 per inch. For example, the screen 22 sized at 40 mesh contains 40 apertures 24 per inch. There are several limitations on the size of the screen 22. A lower mesh number means larger apertures thereby requiring stiffer strands 23 of the screen 22. If the mesh number is too low, the screen 22 becomes too difficult to cut in the manufacture, and too difficult to flex in operation. A higher mesh number means smaller apertures and thinner strands 23. If the mesh number is too high, the screen 22 is too flexible, and the activator 20 can activate prematurely. It has been found that the apertures 24 corresponding to a screen size of 40 to 50 mesh are most suitable, with a size of 40 mesh preferable because of an attractive price and suitable rigidity. Other sizes have also been found to be effective. Preferably, the screen 22 is cut to a one-inch round shape to minimize sharp edges. In the alternative, an oval shape or a square or a rectangular shape of sizes smaller or larger than one-inch may also be used with the invention.

The abrasive particles 26 are most preferably comprised of Aluminum Oxide, but other abrasive particulate matter is also effective, such as quartz, silica or garnet. Preferably, the abrasive particles 26 exhibit a hardness of six or greater on the Mohs scale.

Of substantial importance to the operation of the activator 20 is the relationship between the size of the abrasive particles 26 and the size of the screen 22. Once the size of the screen 22 has been selected, then the size of the abrasive particles 26 can be determined.

Just as screen size is measured by mesh, the abrasive particle size is measured by grit. The higher the grit number the finer the grit. For example, the abrasive particles 26 sized at 220 grit will pass through the screen 22 sized at 220 mesh.

The abrasive particles 26 must be sized relative to the screen size. There is a relationship between mesh size and the size of the abrasive particles 26. The abrasive particle 26 must be small enough to allow the abrasive particle to come into contact with both the warp 23A and the weave 23B of the screen 22. Once the screen size is selected, the abrasive particles 26 must be sized to provide good contact with the screen 22. Also, finer grit is more expensive.

Considering these factors, it has been found that the abrasive particles 26 having a diameter of not larger than one third the diameter of the apertures 24 and not smaller than one fifteenth the diameter of the apertures 24 are suitable for this function. More particularly, a size of substantially one fourth the size of the screen mesh is most preferable. The abrasive particles 26 having a size of not larger than 120 grit and not smaller than 600 grit have been found to be appropriate for the screen 22 sized at 40 mesh. Most specifically, it has been found that a 40 mesh stainless steel screen 22, and 220 grit aluminum oxide abrasive particles 26 appears to be an optimum condition.

Once the composition and the size has been determined, abrasive particles 26 are affixed to the strands 23 of the screen 22 within the apertures 24 by an adhesive agent (not shown). FIG. 9 shows four adjacent strands 23 of the screen 22 and the abrasive particles 26 mounted therebetween.

Figure 11:
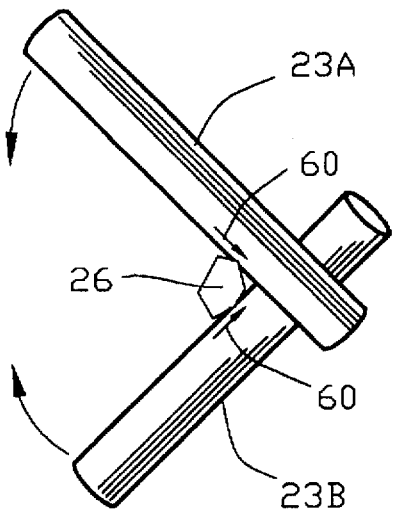
FIG. 11 illustrates the movement of two adjacent strands of the screen and the resultant forces exerted on the activation material in contact with both strands.

In the manufacturing process, described more fully hereinafter, rollers force the abrasive particles 26 into the activator 20, so there is good contact with the warp 23A and the weave 23B of the screen 22, Preferably, numerous abrasive particles 26 are in contact with warp 23A and the weave 23B of the screen 22 as shown in FIG. 11. The screen 22 and the abrasive particles 26 define a plurality of contact interfaces 70. The contact interfaces 70 define a plurality of planes (not shown).

An adhesive agent (not shown) is used for adhering the abrasive particles 26 to the screen 22. Sodium silicate "D" has been found to be an effective adhesive agent for adhering the abrasive particles 26 to the screen 22. Other adhesives, such as shellack may also be used, but are not considered as reliable.

The lamination 28 also assists in maintaining the adherence of the abrasive particles 26 to the screen 22. The lamination 28 is affixed to the screen 22, substantially enclosing the screen 22 and the abrasive particles 26. The lamination 28 thus adds rigidity and thereby inhibits flexing action of the screen 22, and detachment of the abrasive particles 26. Scotch brand "Magic" one-inch tape is the preferred material for the lamination 28. Canoba wax or shellac may also be used.

The process of manufacturing the activator 20 comprises cutting of 316 stainless steel 40-mesh screen 22 into four-inch strips using a break shear. A pneumatic press is used to punch out one-inch diameter slugs from the four-inch strips, thus creating the screen 22 in a round or oval shape. The screen 22 is then placed in a sodium silicate solution comprising 50 percent "D" sodium silicate and 50 percent water. The excess liquid is drained off, and the screens 22 are placed in a plastic shaker containing the abrasive particles 26 comprising aluminum oxide 220 grit blasting media. One part of aluminum oxide to three parts slugs is used. The plastic shaker is then agitated. The slugs are passed through rubber rollers to force the aluminum oxide tightly into the slugs so that numerous abrasive particles 26 are in secure contact with the warp and the weave 23A and 23B of the screen 22 as shown in FIG. 11. The slugs are then placed in a cabinet heated to 120 degrees F., and left overnight to dry. The slugs are then sandwiched between two layers of one-inch wide Scotch brand magic tape, and the excess tape is trimmed away. The completed activator 20 is then placed in the flexible container 40 containing supersaturated solution 30, and the flexible container 40 is sealed.

Operation of the activator 20 can be accomplished quickly, easily and reliably. As show in FIG. 2, the activator 20 is pinched between the thumb and forefinger of each hand of an operator through the flexible container 40. A flexing movement initiates the formation of crystals 32 from the solution 30, as shown in FIG. 3. Very quickly thereafter, the crystals 32 have formed throughout the supersaturated solution 30, resulting in the release of heat 50, as shown in FIG. 4.

The precise mechanism by which the flexing of the activator 20 initiates crystallization on a molecular basis is not certain. However, it is believed that crystallization is initiated by shearing forces 60 exerted between two hard objects, specifically the stainless steel strands 23 of the screen 22 and the aluminum oxide abrasive particles 26, as more fully described hereinafter.

Figure 10:
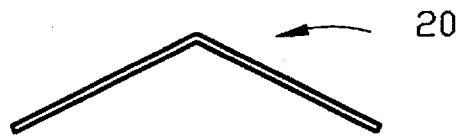
FIG. 10 is a representation of the improved activator in FIG. 7 in a flexed position.
Figure 12:
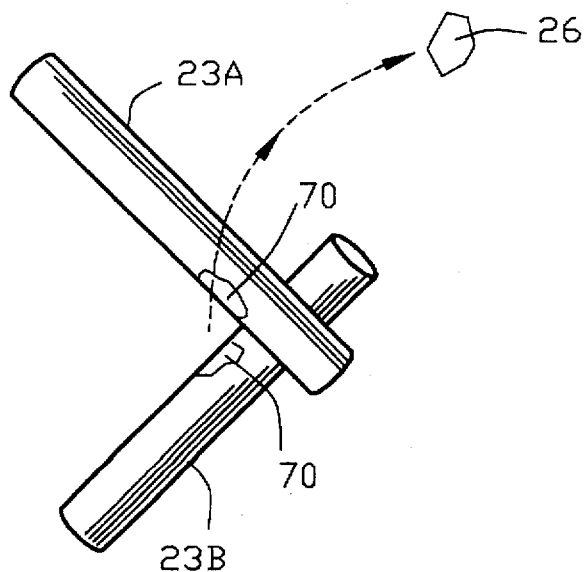
FIG. 12 illustrates the activation material separating from the strands of the screen.

Upon flexing as described above, the activator 20 assumes a bent position as shown in FIG. 10. Because the screen 22 is comprised of relatively flexible strands 23, two adjacent warp and weave strands 23A and 23B move independently of one another, as represented in FIG. 11. Since the abrasive particle 26 is in contact with both moving warp and weave strands 23A and 23B, such independent movement results in shearing forces 60 being applied between the warp and weave strands 23A and 23B, and the abrasive particle 26. Because of the hardness and relative inflexibility of the abrasive particle 26, no movement is possible thereby resulting in the shearing at contact interface 70 and the separation of the abrasive particle 26 from the warp and weave strands 23A and 23B, as shown in FIG. 12. It is believed that such shearing forces 60 cause one of the molecules of solution 30 to fracture resulting in the initiation of crystallization. More specifically, it is believed that an anhydrous molecule from the supersaturated solution 30 of sodium acetate trihydrate is sheared from the sodium acetate trihydrate and crystallization occurs.

By encapsulating the screen 22 and the abrasive particles 26 with the laminate 28, the lamination 28 serves two functions in the operation of activator 20. The primary function of the lamination 28 is to prevent inadvertent initiation of crystallization. By adding rigidity, the lamination 28 inhibits the flexing action of the screen 22 thereby reducing the likelihood of activation. Devices of this type disclosed by prior art are notoriously "trigger happy". Twenty to thirty percent pro-activation in shipment due to motion is not uncommon in the industry. As such, the inhibiting effect of the lamination 28 is important in ensuring commercial viability of the device.

The second function of the lamination 28 is to protect the flexible container 40 from punctures by sharp strands 23 of the screen 22. Such punctures also reduce profitability.

It is believed that this explanation is correct. However, it should be understood that this explanation is offered to provide insight as to the cause for the ultimate result. It is not intended to constitute a limitation. The attainment of the result is the important factor, not the explanation as to how the result was attained.

The present invention overcomes the aforementioned inadequacies of the prior art by providing a simple, effective and reliable trigger at low cost. First, it is simple to manufacture. Its component parts are inexpensive and readily available. The manufacturing process entails few steps, each of which is simple and not requiring highly expensive machinery to complete. Moreover, the device is simple to operate. Merely flexing the screen is sufficient to actuate the device. Second, the trigger is inexpensive to produce. Because of the simple composition, each trigger costs only pennies to manufacture. Also, it is effective in the initiation of crystallization. Very few flexes are sufficient to actuate, sometimes as few as one. Finally, the new device is reliable in producing crystallization upon demand. Moreover, it is equally reliable in not activating inadvertently.

The present invention offers several advantages over the prior art. First, it is simple both in design and manufacture, constructed of readily available materials such as screens, abrasive material, and scotch tape. Because of the simplicity, it is also inexpensive to produce and transport. Inexpensive to produce because of inexpensive components and a simple manufacturing process, as described previously. Inexpensive to transport because no special packing is needed, and because there is practically no loss of product due to premature activation.

Activator 20 is also highly effective and reliable in initiating crystallization. Very few flexes are required. This efficacy is due to the unique design of the present invention as compared to prior art. Since contact interfaces 70 exist at multiple locations on screen 22, the opportunity and likelihood exists that such shearing occurs simultaneously at multiple locations, thereby greatly increasing the likelihood of the initiation of crystallization with few flexes and thereby greatly increasing the effectiveness of activator 20. This feature explains one of the advantages of employing screen 22 in activator 20 as compared to prior art employing a metal plate upon which abrasive particles 26 are adhered. In addition, screen 22 is more flexibility than a metal plate, and provides for contact interfaces 70 which are not substantially in the same plane. These features provide better opportunity for shearing forces 60 between the metal and abrasive particles 26. Also adding to reliability is lamination 28 which inhibits unintentional initiation of crystallization, especially during shipping and handling. The present invention offers substantial advantages over prior art of activation of crystallization of supersaturated solutions.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An improved activator for initiating crystallization of a supersaturated solution within a flexible container, the activator comprising:
    a flexible screen for immersing in the supersaturated solution within the flexible container;
    said flexible screen defining a plurality of apertures therein; and
    an activation material affixed to said screen within said plurality of apertures, said activation material for interacting with said screen to initiate crystallization of the supersaturated solution upon flexing of said flexible screen.

2. An improved activator as set forth in claim 1, wherein said screen and said activation material define a plurality of contact interfaces therebetween for creating a shearing action between said screen and said activation material upon flexing of said screen.

3. An improved activator as set forth in claim 2, wherein said plurality of contact interfaces define a plurality of planes for allowing non-parallel forces to be simultaneously exerted by said screen on said activation material upon flexing of said screen.

4. The improved activator of claim 1, wherein said screen is of a size of not less than 40 and not greater than 50 mesh.

5. The improved activator of claim 1, further comprising an adhesive agent for adhering said activation material to said screen.

6. The improved activator of claim 1, further comprising a lamination affixed to said screen for inhibiting the initiation of crystallization.

7. The improved activator of claim 1, wherein said activation material comprises particles having a diameter not larger than one third the diameter of said apertures and not smaller than one fifteenth the diameter of said apertures.

8. The improved activator of claim 1, wherein said activation material comprises particles having a size of not larger than 120 grit and not smaller than 600 grit.

9. The improved activator of claim 1, wherein said activation material exhibits a hardness of six or greater on the Mohs scale.

10. An improved activator for initiating crystallization of a supersaturated solution within a flexible container, the activator comprising:
    a flexible screen for immersing in the supersaturated solution within the flexible container;
    said screen comprising a plurality of interwoven strands;
    an activation material affixed to said screen;
    said activation material comprising a plurality of abrasive particles;
    at least one of said abrasive particles having contact interfaces with at least two of said strands of said screen; and
    said contact interfaces for allowing interaction between said abrasive particles and said strands to initiate crystallization of the supersaturated solution upon flexing of said flexible screen.

11. The improved activator of claim 10, wherein said contact interfaces define a plurality of planes for allowing non-parallel forces to be simultaneously exerted by said strands on said abrasive particles upon flexing of said screen.

12. The improved activator of claim 10, wherein said screen is of a size of not less than 40 and not greater than 50 mesh.

13. The improved activator of claim 10, further comprising an adhesive agent for adhering said activation material to said screen.

14. The improved activator of claim 10, further comprising a lamination affixed to said screen for inhibiting the initiation of crystallization.

15. The improved activator of claim 10, wherein said abrasive particles have a diameter not larger than one third the size of the mesh of the said screen, and not smaller than one fifteenth the size of the mesh of the said screen.

16. The improved activator of claim 10, wherein said abrasive particles have a size of not larger than 120 grit and not smaller than 600 grit.

17. The improved activator of claim 10, wherein said abrasive particles exhibit a hardness of six or greater on the Mohs scale.

18. The method of making an improved activator for initiating crystallization of a supersaturated solution in a flexible container, comprising the steps of:
    cutting a slug from a screen;
    placing the slug in sodium silicate solution;
    draining of excess sodium silicate solution;
    placing the slug and abrasive particulate in a shaker;
    agitating the shaker;
    mechanically pressing abrasive particulate tightly into the slug;
    drying the slug; and
    laminating the slug.

* * * * *